US012083229B2

(12) United States Patent
Hossain et al.

(10) Patent No.: US 12,083,229 B2
(45) Date of Patent: Sep. 10, 2024

(54) OCULAR DRUG DELIVERY FORMULATION

(71) Applicant: INMED PHARMACEUTICALS INC., Vancouver (CA)

(72) Inventors: Sazzad Hossain, Richmond (CA); Maryam Kabiri, Vancouver (CA); Vikramaditya Ganapati Yadav, Vancouver (CA)

(73) Assignee: INMED PHARMACEUTICALS INC., Vancouver (CA)

( * ) Notice: Subject to any disclaimer, the term of this patent is extended or adjusted under 35 U.S.C. 154(b) by 1090 days.

(21) Appl. No.: 16/611,837

(22) PCT Filed: May 8, 2018

(86) PCT No.: PCT/CA2018/050548
§ 371 (c)(1),
(2) Date: Nov. 7, 2019

(87) PCT Pub. No.: WO2018/205022
PCT Pub. Date: Nov. 15, 2018

(65) Prior Publication Data
US 2020/0163900 A1    May 28, 2020

Related U.S. Application Data

(60) Provisional application No. 62/503,258, filed on May 8, 2017.

(51) Int. Cl.
| | |
|---|---|
| *A61K 9/51* | (2006.01) |
| *A61K 9/00* | (2006.01) |
| *A61K 31/192* | (2006.01) |
| *A61P 27/02* | (2006.01) |
| *A61P 27/06* | (2006.01) |
| *B82Y 5/00* | (2011.01) |

(52) U.S. Cl.
CPC .......... *A61K 9/5161* (2013.01); *A61K 9/0048* (2013.01); *A61K 9/5153* (2013.01); *A61K 31/192* (2013.01); *B82Y 5/00* (2013.01)

(58) Field of Classification Search
CPC .. A61K 9/5161; A61K 31/192; A61K 9/0048; A61K 9/5153; A61P 27/02; A61P 27/06; B82Y 5/00
See application file for complete search history.

(56) References Cited

U.S. PATENT DOCUMENTS

| | | | |
|---|---|---|---|
| 8,758,826 B2 | 6/2014 | Bevier et al. | |
| 9,205,046 B2 * | 12/2015 | Shoichet | A61K 38/1866 |
| 2013/0316006 A1 * | 11/2013 | Popov | A61P 27/02 |
| | | | 424/490 |
| 2018/0098948 A1 | 4/2018 | Small-Howard et al. | |

FOREIGN PATENT DOCUMENTS

| | | | | |
|---|---|---|---|---|
| CN | 103040888 A | * | 4/2013 | ........... A61K 31/045 |
| WO | WO 2018/205038 A1 | | 11/2018 | |

OTHER PUBLICATIONS

Husni et al.; Med Chem Res. 23(9): 4295-4300. Published Sep. 1, 2014.*
Zirpel et al.; Biotechnol Lett.; 37(9): 1869-1875. Published online: May 21, 2015.*
Macrae et al.; Am J Ophth.; vol. 95, Iss 3; pp. 332-341 (Abstract only). Published Mar. 1983.*
Caicco M. J. et al., "Characterization of hyaluronan-methylcellulose hydrogels for cell delivery to the spinal cord", Journal of Biomaterials research Part A, vol. 101A, pp. 1472-1477 (2013).
Durán-Lobato, M. et al., "Comparative study of chitosan- and PEG-coated lipid and PLGA nanoparticles as oral delivery systems for cannabinoids", Journal of Nanoparticle research, vol. 17, pp. 1-17 (2015).
Gaudana et al, "Recent Perspectives in Ocular Drug Delivery", Pharmaceutical Research, Kluwer Academic Publishers—Plenum Publishers, NL, vol. 26, No. 5, pp. 1197-1216 (2008).
Ludwig, A. et al., "The use of mucoadhesive polymers in ocular drug delivery", Advanced Drug Delivery Review, vol. 57, pp. 1595-1639 (2005).
Mayol, L et al., "Effect of hyaluronic acid on the thermogelation and biocompatibility of its blends with methyl cellulose", Carbohydrate Polymers, vol. 112, pp. 480-485 (2014).
Punyamurthula et al, "Ocular Disposition of [increment]8-Tetrahydrocannabinol from Various Topical Ophthalmic Formulations", AAPS Pharmscitech, Springer US, New York, vol. 18, No. 6, pp. 1936-1945 (2016).
Wang, Y. et al., "Accelerated release of a sparingly soluble drug from an injectable hyaluronan-methylcellulose hydrogel", Journal of Controlled Release, vol. 140, pp. 218-223 (2009).

* cited by examiner

*Primary Examiner* — Jeffrey T. Palenik
(74) *Attorney, Agent, or Firm* — Todd Lorenz

(57) ABSTRACT

There is provided an ocular drug delivery formulation comprising a delivery carrier comprising a cellulosic polymer and an anionic polysaccharide and nanoparticles comprising an amphiphilic non-ionizable block copolymer and a cannabinoid. The formulation has a gel point of about 30° C. to about 37° C.

7 Claims, 7 Drawing Sheets

OCULAR DRUG DELIVERY FORMULATION

TECHNICAL FIELD

The technology relates to nanoparticle drug delivery systems. In particular the technology relates to a drug delivery formulation of a thermally sensitive delivery carrier and a drug carrying nanoparticle for the treatment of eye disorders.

BACKGROUND

Glaucoma is a chronic optic neuropathy that is caused by high intraocular pressure. Inadequate or obstructed drainage of the aqueous humor through the trabecular mesh increases the fluid pressure within the anterior chamber, subsequently propagating into the posterior chamber of the eye. Increased intraocular pressure results in thinning of the basal membrane of the retina and damages the head of the optic nerve. Glaucoma is currently the leading cause of blindness worldwide and it is estimated to affect a population close to 80 million by 2020.

Current glaucoma remedies function to lower intraocular pressure either by inhibiting carbonic anhydrase in the eye, or reducing the production of aqueous humor by the ciliary epithelial cells, or by increasing fluid drainage through the trabecular mesh. There is room for improvement for existing pharmacologically active agents, most of which are formulated as eye drops, as it has been shown that less than 5% of the dose penetrates the cornea after eye drop administration.

Although the role of cannabinoids in treating glaucoma is very well known, no cannabinoid based product for the treatment of eye disorders such as glaucoma currently exist in the market. The neuroprotective properties of cannabinoids have been extensively studied in different neurodegenerative pathologies such as Parkinson's disease, Huntington's disease and multiple sclerosis. Cannabinoids have low aqueous solubility which results in poor bioavailability. Hence, neuroprotection as a therapeutic strategy in eye disorders has not been pursued due to the difficulties associated with the targeted delivery of cannabinoids to intraocular tissues. Previous attempts at topical delivery of cannabinoids to human ocular tissues are limited to the use of mineral oil and cyclodextrins as vehicles for the cannabinoid. However, the success of these attempts been limited because of the ocular irritancy and cytotoxicity of these vehicles More generally there is considerable room for improvement for existing drugs for eye disorders, most of which are formulated as eye drops. It is known that when the drugs are delivered as drops, less than 5% of the dose penetrates the cornea after eye drop administration.

The present inventors have developed a thermally sensitive, nanoparticle-laden delivery carrier for spatiotemporal and dosage-controlled release of cannabinoids into the eye.

SUMMARY

In a first aspect, there is provided an ocular drug delivery formulation comprising:
- a delivery carrier comprising a cellulosic polymer and an anionic polysaccharide; and
- nanoparticles comprising an amphiphilic non-ionizable block copolymer and a poorly water soluble or immiscible pharmacologically active agent;

wherein the formulation has a gel point of about 30° C. to about 37° C., preferably wherein the pharmacologically active agent is a cannabinoid.

The cellulosic polymer may be selected from the group consisting of methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, hydroxypropyl methylcellulose acetate, hydroxypropyl methylcellulose propionate, hydroxypropyl methylcellulose butyrate, carboxymethylcellulose and any mixture thereof.

In one embodiment the cellulosic polymer is methylcellulose.

The concentration of the cellulosic polymer may be from about 0.2 wt % to about 10 wt % of the formulation, preferably from about 0.5 wt % to about 6 wt %, more preferably from about 1 wt % to about 4 wt %, more preferably from about 1 wt % to about 3 wt %, or about 2.5 wt %.

The anionic polysaccharide may be selected from the group consisting of hyaluronic acid, derivatives of hyaluronic acid, alginate, derivatives of alginate and any mixture thereof.

In one embodiment the anionic polysaccharide is hyaluronic acid.

The concentration of the anionic polysaccharide may be from about 0.1 wt % to about 10 wt % of the formulation, preferably from about 0.2 wt % to about 5 wt %, more preferably from about 0.5 wt % to about 2.5 wt %, more preferably from about 1 wt % to about 2 wt %, or about 1.5 wt %.

The amphiphilic non-ionizable block copolymer may be selected from the group consisting of poly(ethylene oxide-b-ε-caprolactone) (also known as poly(ε-caprolactone-b-ethylene glycol) or pCL-PEG), poly(ethylene oxide-b-lactide), poly(lactide-b-ethylene glycol), poly(ethylene oxide-b-glycolide), poly(glycolide-b-ethylene glycol), poly(ethylene oxide-b-lactide-co-glycolide), poly(lactide-co-glycolide-b-ethylene glycol), and mixtures thereof.

In one embodiment the amphiphilic non-ionizable block copolymer is poly(ethylene oxide-b-lactide).

In an embodiment, the cannabinoid is CBGA.

The cannabinoid may be selected from the group consisting of cannabigerolic acid (CBGA); cannabigerolic acid monomethylether (CBGAM), cannabigerol (CBG), cannabigerol monomethylether (CBGM), cannabigerovarinic acid (CBGVA), cannabichromevarin (CBCV), cannabichromenic acid (CBCA) cannabichromene (CBC), cannabidiolic acid (CBDA), cannabidiol (CBD), cannabidiol monomethyl ether (CBDM), cannabidiol-C4 (CBD-D4), cannabidivarinic acid (CBDVA), cannabidivarin (CBDV), cannabidiorcol (CBD-D1), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid C4 (THCA-C4), delta-9-tetrahydrocannabinol-C4 (THC-C4), delta-9-tetrahydrocannabivarinic acid (THCVA), delta-9-tetrahydrocannabivarin (THCV), delta-9-tetrahydrocannabiorcolic acid (THCA-C1),), delta-9-tetrahydrocannabiorcol (THC-C1), delta-7-cis-iso-tetrahydrocannabivarin (D7-THCV), delta-8-tetrahydrocannabinolic (D8-THCA), delta-8-tetrahydrocannabinol (D8-THC), cannabicycloic acid (CBLA), cannabicyclol (CBL), cannabicyclovairn (CBLV), cannabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-C4 (CBN-C4), cannabinol-C2 (CBN-C2), cannabivarin (CBV), cannabiorcol (CBN-C1), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CBTVE), dehydrocannabifuran (DCBG), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxy-alpha-alpha-2-trimethyl-9-n-propyl-2,6-methano-2H-1-benzoxoxin-5-methanol (OH-iso-HHCV), cannabiripsol (CBR), and trihydroxy-delta-9-tetrahydrocannabinol (triOH-THC).

In one embodiment the cannabinoid is cannabigerolic acid (CBGA).

The nanoparticles may have an average diameter of between about 400 nm to 500 nm, between about 300 nm to 400 nm, between about 200 nm to 300 nm, between about 100 nm to 200 nm or between about 25 nm to 100 nm. In some embodiments, the nanoparticles have an average diameter of from about 50 nm to about 300 nm, from about 75 nm to about 250 nm, from about 100 nm to 250 nm, or about 200 nm. In some embodiments, the nanoparticles have an average diameter of from about 175 nm to about 200 nm.

The gel point of the formulation may be about 30° C., 30.25° C., 30.50° C., 30.75° C., 31° C., 31.25° C., 31.50° C., 31.75° C., 32° C., 32.25° C., 32.50° C., 32.75° C., 33° C., 33.25° C., 33.50° C., 33.75° C., 34° C., 34.25° C., 34.50° C., 34.75° C., 35° C., 35.25° C., 35.5° C., 35.75° C., 36° C., 36.25° C., 36.5° C., 36.75° C., or about 37° C. In some embodiments, the gel point of the formulation is from about 30° C. to about 35° C., more preferably from about 30° C. to about 34° C., or about 32° C.

In some embodiments the concentration of cellulosic polymer and the average diameter of the nanoparticles determines the gel point of the formulation.

In a second aspect there is provided an ocular drug delivery formulation comprising:
 a delivery carrier comprising methyl cellulose and hyaluronic acid; and
 nanoparticles comprising poly(ethylene oxide-b-lactide) and a poorly water soluble or immiscible pharmacologically active agent;
 wherein the formulation has a gel point of about 30° C. to about 37° C., preferably wherein the pharmacologically active agent is cannabigerolic acid (CBGA).

In a third aspect there is provided an ocular drug delivery formulation comprising:
 a delivery carrier comprising 2.5 wt % methyl cellulose and 1.5 wt % hyaluronic acid; and
 nanoparticles comprising poly(ethylene oxide-b-lactide) and a poorly water soluble or immiscible pharmacologically active agent preferably wherein the pharmacologically active agent is cannabigerolic acid (CBGA);
 wherein the average diameter of the nanoparticles is about 175 nm-200 nm; and wherein the formulation has a gel point of about 32° C.

In a fourth aspect there is provided a method of treatment of an eye disorder comprising administering an effective amount of a formulation of any one of the first to third aspects to the eye of a subject in need thereof. The eye disorder may be glaucoma.

In a fifth aspect there is provided a use of the formulation of any one of the first to third aspects for the treatment of an eye disorder. The eye disorder may be glaucoma.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

DEFINITIONS

Figure 1:
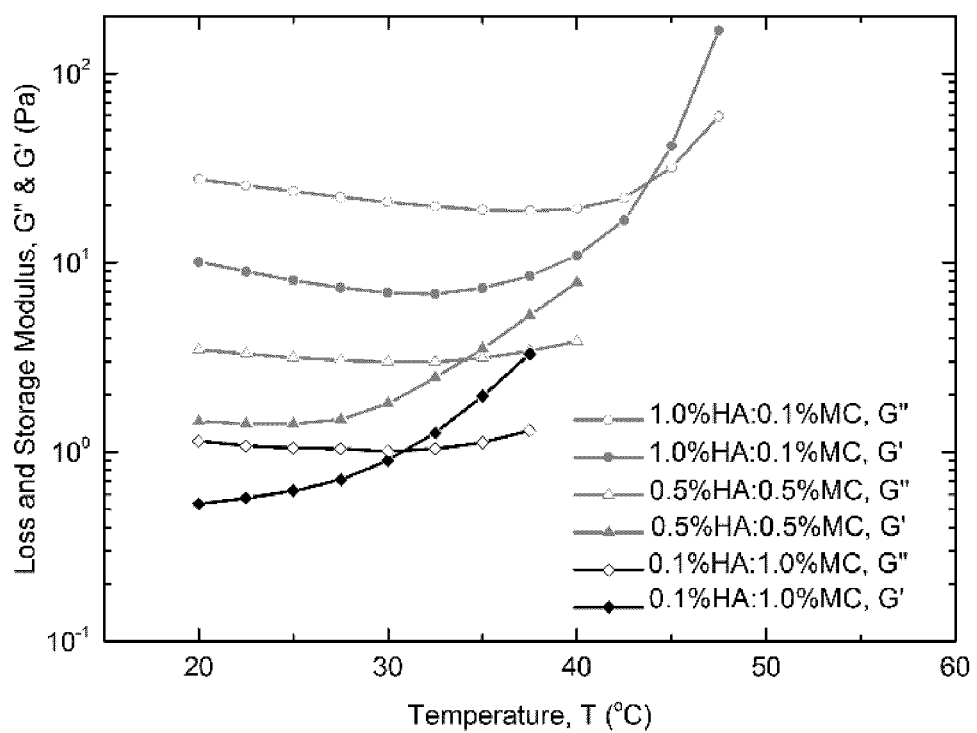
FIG. 1. Loss (G", unfilled symbols) and storage (G', filled symbols) moduli as a function of temperature for delivery carriers with different weight ratios of Hyaluronic Acid (HA) and Methyl Cellulose (MC). All experiments were performed at 1 Hz using a rheometer with cone and plate geometry.

As used herein the term 'poorly water soluble' refers to any substance that has a solubility in water of less than 5 mg/ml at 25° C. The utility of the invention increases as the water solubility of the cannabinoid decreases. The cannabinoid may have an even lower solubility in water, such as less than about 1 mg/mL, less than about 0.1 mg/mL, and even less than about 0.01 mg/mL.

As used herein, the term 'immiscible' means that the solvent has a solubility in the aqueous solution of less than about 10 wt %, or less than about 5 wt %, or less than about 3 wt %.

As used herein the term 'delivery carrier' refers to a composition of comprising at least one of a broad class of natural or synthetic polymeric materials, which have an affinity for an aqueous medium, and are able to absorb large amounts of the aqueous medium, but which do not normally dissolve in the aqueous medium. A delivery carrier may be liquid at some temperatures and form a gel at a particular temperature.

The term 'eye disorder' as used herein refers to any ocular disease including glaucoma, scleritis, Graft-versus-Host Disease (GvHD), keratitis, corneal ulcer, corneal abrasion, snow blindness, Thygeson's superficial punctuate keratopathy, corneal neovascularization, Fuch's dystrophy, keratoconus, keratoconjunctivitis sicca (dry eye), iritis, corneal anesthesia, neurotrophic keratopathy, red eye, pink eye, keratomycosis, xeropthalmia, retinoblastoma, uveitis, pterygium, keratopathy, macular degeneration, Stargardt disease, Retinitis pigmentosa, and pingueculae.

In embodiments described herein, certain numerical values and ranges are specified for various parameters such as wt %, gel point, pH, and/or nanoparticle diameter. Such specified values and/or ranges may be varied ±10% unless otherwise indicated.

DESCRIPTION OF EMBODIMENTS

Formulations

The formulations described herein comprise an aqueous solution of a cellulosic polymer and an anionic polysaccharide that forms a gel at about 30° C. to about 37° C. or higher. In addition the formulations contain a nanoparticle comprising an amphiphilic non-ionizable block copolymer and a pharmacologically active agent.

The nanoparticle-delivery carrier can be packaged as a liquid and applied as an eye drop to a patient. Once in contact with the eye its temperature will be elevated to the temperature of the eye and the liquid will form a gel. A liquid formulation permits easy dosing, simplifies manufacturing and simplifies the path towards development of a regulated industrial-scale manufacturing process.

In one method of use, the formulation is maintained at a temperature of less than its gel point (for example less than the gel-point of about 30° C. to about 37° C.) to keep it in a liquid state before being administered to the body. For example, when the formulation is administered to the surface of the eye it forms a hydrogel when it reaches the temperature of the eye surface (about 32° C.).

Alternatively the formulation can be brought to a temperature of about 30° C. to about 37° C. to form a gel and then administered to the body. For example the formulation may be loaded into a syringe as a liquid, warmed in the syringe to form a gel, and administered from the syringe as a gel. Alternatively the composition may be in the gel state when it is loaded into the syringe.

Typically the pH of the formulations in the range of 6.6-7.8. The natural pH of tear fluid is 7.4; however, the formulations will not clause discomfort to a subject as long as the pH of the administered formulation stays in the range of 6.6-7.8 (Sampath Kumar et al., "Recent Challenges and Advances in Ophthalmic Drug Delivery System," in The Pharma Innovation, Vol. 1, No. 4 (2012)).

In other embodiments the solution additionally comprises a stabilizer, preservative, antioxidant, buffer or combination thereof appropriate for use with the cannabinoid.

Nanoparticles

The nanoparticles may be formed by any process that results in formation of nanoparticles of a pharmacologically active agent that is immiscible, poorly water soluble, and/or has a log octanol:water partition coefficient (log $P_{ow}$) of at least 4, such as a cannabinoid, and an amphiphilic, non-ionizable block copolymer. For example, the nanoparticles can be formed by a precipitation or an emulsification process.

In the case of use of a hydrophilic drug, the delivery system may not use any nanoparticles. Instead, the molecules can be directly solubilized into the hydrogel. The method of preparation of the hydrogel will remain unchanged from before. Time-dependent delivery of drug will be ensured through gradual solubilisation of the hydrogel in the tear fluid.

Preferably, the nanoparticles are formed by a precipitation process. In one embodiment of this process, the pharmacologically active agent (e.g., cannabinoid) and amphiphilic non-ionizable block copolymer are first dissolved in a solvent that is immiscible with an aqueous solution in which the pharmacologically active agent (e.g., cannabinoid) and block copolymer are poorly soluble. In some embodiments this organic solution is sonicated. The organic solution is then mixed with the aqueous solution causing the nanoparticles to precipitate.

Suitable amphiphilic non-ionizable block copolymer may be selected from the group comprising poly(ethylene oxide-b-ε-caprolactone) (also known as poly(ε-caprolactone-b-ethylene glycol) or pCL-PEG), poly(ethylene oxide-b-lactide), poly(lactide-b-ethylene glycol), poly(ethylene oxide-b-glycolide), poly(glycolide-b-ethylene glycol), poly(ethylene oxide-b-lactide-co-glycolide), poly(lactide-co-glycolide-b-ethylene glycol), and mixtures thereof. In some embodiments the amphiphilic non-ionizable block copolymer is poly(ethylene oxide-b-lactide).

Solvents suitable for forming the solution of dissolved pharmacologically active agent, and amphiphilic non-ionizable block copolymer can be any compound or mixture of compounds in which the pharmacologically active agent (e.g., cannabinoid) and block copolymer are mutually soluble and which is miscible in the aqueous solution. Examples of suitable solvents include acetone, ethyl acetate, methanol, ethanol, tetrahydrofuran and dimethylsulfoxide (DMSO). Mixtures of solvents, such as 50% ethyl acetate and 50% acetone, can also be used, where the pharmacologically active agent, polymer, and block copolymer are sufficiently soluble to dissolve the pharmacologically active agent (e.g., cannabinoid) and polymer. In one embodiment the solvent is ethyl acetate, methanol, acetone, and mixtures thereof. In another embodiment the solvent is ethyl acetate.

The aqueous solution may be any compound or mixture of compounds in which the pharmacologically active agent (e.g., cannabinoid) and block copolymer are sufficiently insoluble so as to precipitate to form nanoparticles. Suitable aqueous solutions can include saline, buffered saline or water. In an embodiment the aqueous solution is water.

The organic solution and aqueous solution are mixed. For example, the mixing can be by addition of a bolus or stream of organic solution to a container of the aqueous solution, which may be stirred, such that when the nanoparticles precipitate a suspension of nanoparticles is formed in the aqueous solution.

The organic solution:aqueous solution volume ratio can be selected such that there is sufficient aqueous solution in the nanoparticle suspension that the nanoparticles do not rapidly aggregate. However, an excess of aqueous solution may result in a very dilute suspension of nanoparticles, which may require further processing for ultimate use. Generally, the organic solution:aqueous solution volume ratio should be at least 1:100 and 1:2 (organic solution: aqueous solution). In some embodiments, the organic solution:aqueous solution volume ratio ranges from about 1:20 to about 1:5. Preferably, an organic solution:aqueous solution volume ratio of about 1:10.

An alternative process to form the nanoparticles is emulsification. In this process, the pharmacologically active agent (e.g., cannabinoid) and the amphiphilic non-ionizable block copolymer are dissolved in an organic solvent that is immiscible with an aqueous solution in which the pharmacologically active agent (e.g., cannabinoid) and amphiphilic non-ionizable block copolymer are poorly soluble, forming an organic solution. Solvents suitable for forming the solution of dissolved pharmacologically active agent (e.g., cannabinoid) and polymer can be any compound or mixture of compounds in which the pharmacologically active agent (e.g., cannabinoid) and the polymer are mutually soluble and which is immiscible with the aqueous solution. Exemplary solvents include methylene chloride, trichloroethylene, trichloro-trifluoroethylene, tetrachloroethane, trichloroethane, dichloroethane, dibromoethane, ethyl acetate, phenol, chloroform, toluene, xylene, ethyl-benzene, benzyl alcohol, creosol, methyl-ethyl ketone, methyl-isobutyl ketone, hexane, heptane, ether, and mixtures thereof. In one embodiment the solvent is methylene chloride, ethyl acetate, benzyl alcohol, and mixtures thereof. In another embodiment the solvent is ethyl acetate. Suitable aqueous solutions can include saline, buffered saline or water. The aqueous solution is preferably water. In an embodiment the aqueous solution is water.

The organic solution is mixed with the aqueous solution and homogenized to form an emulsion of fine droplets of the organic solution distributed throughout the aqueous phase. The volume ratio of organic solution to aqueous solution used in the process will generally range from 1:100 (organic solution:aqueous solution) to 1:1 (organic solution:aqueous solution). In one embodiment the organic solution:aqueous solution volume ratio ranges from 1:10 to 1:5 (organic solution:aqueous solution).

The emulsion is generally formed by a two-step homogenization procedure. The organic solution and aqueous solution are first mixed using a rotor/stator or similar mixer to create a "pre-emulsion". This mixture is then further processed with a high-pressure homogenizer that subjects the droplets to very high shear, creating a uniform emulsion of very small droplets. A portion of the organic solvent is then removed forming a suspension of the nanoparticles in the aqueous solution. Exemplary processes for removing the organic solvent include evaporation, extraction, diafiltration, pervaporation, vapor permeation, distillation, and filtration. In an embodiment, the organic solvent is removed to a level that is acceptable according to The International Committee on Harmonization (ICH) guidelines. The concentration of solvent in the nanoparticle suspension may be less than the solubility of the solvent in the aqueous solution. Even lower concentrations of solvent are suitable. Thus, the concentration of organic solvent in the nanoparticle suspension may be less than about 5 wt %, less than about 3 wt %, less than about 1 wt %, and even less than about 0.1 wt %.

Once the nanoparticle suspension is made (either by precipitation or emulsification), a portion of the organic solvent is removed from the suspension using methods known in the art. Exemplary processes for removing the organic solvent include evaporation, extraction, diafiltration, pervaporation, vapor permeation, distillation, and filtration, for example ultrafiltration. Typically the recovered nanoparticles are washed with an aqueous solution, for example water. In some embodiments the nanoparticles are recovered by ultrafiltration and washed with water. The solvent may be removed to a level that is acceptable according to FDA or ICH (The International Council on Harmonisation of Technical Requirements for Registration of Pharmaceuticals for Human Use) guidelines. For example the concentration of organic solvent in the nanoparticle suspension may be less than about 10 wt %, less than about 9 wt %, less than about 8 wt %, less than about 7 wt %, and even less than about 6 wt %, less than about 5 wt %, less than about 4 wt %, less than about 3 wt %, %, less than about 2 wt %, less than about 1 wt %, less than about 0.5 wt %, and less than about 0.1 wt %.

In one embodiment the nanoparticles are formed by a process comprising:
  (a) forming an organic solution comprising a poorly water soluble cannabinoid and an amphiphilic non-ionizable block copolymer dissolved in a solvent;
  (b) forming an aqueous solution, wherein the pharmacologically active agent (e.g., cannabinoid) and the amphiphilic non-ionizable block copolymer are poorly soluble in the aqueous solution;
  (c) mixing the organic solution with the aqueous solution to form a mixture; and
  (d) removing the solvent from the mixture to form a suspension comprising the nanoparticles and the aqueous solution.

The nanoparticles may have an average diameter of less than about 500 nm, less than about 400 nm, less than about 300 nm, less than about 200 nm or less than about 100 nm.

In some embodiments the nanoparticles have an average diameter of between about 400 nm to about 500 nm, between about 300 nm to about 400 nm, between about 200 nm to about 300 nm, between about 100 nm to about 200 nm or between about 25 nm to about 100 nm. In one embodiment the nanoparticles have an average diameter of between about 100 nm to about 200 nm. In one embodiment the nanoparticles have an average diameter of between about 175 nm to about 200 nm.

The pharmacologically active agent (e.g., cannabinoid) may be present in any amount suitable for a desired application. For example, the pharmacologically active agent (e.g., cannabinoid) may be present in an amount ranging from less than about 1% to about 90 weight %, relative to the weight of the formulation. A higher or lower concentration of the pharmacologically active agent (e.g., cannabinoid) may be used, and the concentration may vary within the aforementioned range. For example, the pharmacologically active agent (e.g., cannabinoid) may be present in an amount ranging from about 0.01% to about 90%, about 0.01% to about 10%, about 0.2 to about 5%, about 1% to about 10%, about 0.01% to about 10%, about 0.1% to about 10%, about 0.01% to about 5%, about 0.1% to about 5%, about 0.1% to about 3%, less than about 1% to about 50%, less than about 1% to about 30%, less than about 1% to about 80%, about 5% to about 90%, about 10% to about 95%, or about 0.1 to about 5% by weight of the formulation.

Both the emulsion process and the precipitation process result in the formation of a suspension of the nanoparticles in an aqueous solution. In some instances it is desirable to concentrate the nanoparticles or to isolate the nanoparticles in solid form by removing some or all of the liquid from the suspension. Exemplary processes for removing at least a portion of the liquid include spray drying, spray coating, spray layering, lyophilisation, evaporation, vacuum evaporation, filtration, ultrafiltration, reverse osmosis, and other processes known in the art. The liquid may be removed by filtration or ultrafiltration. In one embodiment, the liquid is removed by spray drying. In another embodiment, the liquid is removed by evaporation. In still another embodiment, the liquid is removed by lyophilisation. In yet another embodiment, the liquid is removed by any combination of spray drying, spray coating, spray layering, lyophilisation, evaporation, vacuum evaporation, filtration, ultrafiltration, reverse osmosis, and other processes known in the art.

In some embodiments a material is added to the suspension of nanoparticles prior to removal of the liquids to help slow or prevent aggregation of the nanoparticles as the liquids are being removed. The material may also assist in dispersion of the nanoparticles when they are added to an aqueous solution. The material is typically pharmaceutically acceptable and water soluble. Examples of suitable materials include polyvinyl pyrrolidone (PVP), trehalose, hydroxypropyl methyl cellulose (HPMC), hydroxypropyl cellulose (HPC), casein, caseinate, albumin, gelatin, gum acacia, lactose, mannitol, and other matrix materials know in the art.

Cannabinoids and Other Pharmacologically Active Agents

Any suitable pharmacologically active agent (e.g., cannabinoid) can be used with the formulations. In particular, pharmacologically active agents that are poorly soluble or immiscible in water can be incorporated into the nanoparticles of the formulations for administration to a subject. In some embodiments, the pharmacologically active agent has an log octanol:water partition coefficient (log $P_{ow}$) of at least 4. In some cases, the pharmacologically active agent has a log $P_{ow}$ of from about 4 to about 7, from about 4 to about 6.7, from about 4.5 to about 7, from about 4.5 to about 6.7, from about 5 to about 7, or from about 5 to about 6.7.

In some embodiments the cannabinoid selected from the group comprising cannabigerolic acid (CBGA); cannabigerolic acid monomethylether (CBGAM), cannabigerol (CBG), cannabigerol monomethylether (CBGM), cannabigerovarinic acid (CBGVA), cannabichromevarin (CBCV), cannabichromenic acid (CBCA) cannabichromene (CBC), cannabidiolic acid (CBDA), cannabidiol (CBD), cannabidiol monomethyl ether (CBDM), cannabidiol-$C_4$(CBD-D4), cannabidivarinic acid (CBDVA), cannabidivarin (CBDV), cannabidiorcol (CBD-D1), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid $C_4$ (THCA-C4), delta-9-tetrahydrocannabinol-$C_4$ (THC-C4), delta-9-tetrahydrocannabivarinic acid (THCVA), delta-9-tetrahydrocannabivarin (THCV), delta-9-tetrahydrocannabiorcolic acid (THCA-C1),) delta-9-tetrahydrocannabiorcol (THC-C1), delta-7-cis-iso-tetrahydrocannabivarin (D7-THCV), delta-8-tetrahydrocannabinolic (D8-THCA), delta-8-tetrahydrocannabinol (D8-THC), cannabicycloic acid (CBLA), cannabicyclol (CBL), cannabicyclovairn (CBLV), cannabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-$C_4$ (CBN-C4), cannabinol-$C_2$ (CBN-C2), cannabivarin (CBV), cannabiorcol (CBN-C1), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CBTVE), dehydrocannabifuran (DCBG), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxy-alpha-alpha-2-trimethyl-9-n-propyl-2,6-methano-2H-1-benzoxoxin-5-methanol (OH-iso-HHCV), cannabiripsol (CBR), trihydroxy-delta-9-tetrahydrocannabinol (triOH-THC).

The cannabinoid can be synthetic or derived from a plant. Typically the plant is of the genus Cannabis. Cannabinoids that occur in other plant genera can also be used in the formulations. For example cannabinoinds derived from plants of the generea *Echinacea, Acmella, Helichrysum*, and *Radula* can be used in the formulations. For example the lipophilic alkamides (alkylamides) from *Echinacea* species including the cis/trans isomers dodeca-2E,4E,8Z,10E/Z-tetraenoic-acid-isobutylamide can be used. Other suitable cannabinoids include beta-caryophyllene and anandamide. In one embodiment the cannabinoid is cannabigerolic acid (CBGA). In some embodiments, the pharmaceutically active agents are CBGA, a functional derivative of CBGA, or a combination thereof.

In some embodiments additional pharmacologically active agents or alternative pharmacologically active agents that are not cannabinoids can be included in the nanoparticles. Such non-cannabinoid pharmacologically active agents can be poorly water soluble, immiscible, or have a log $P_{ow}$ of at least about 4 (e.g., from about 4 to about 7, from about 4 to about 6.7, from about 4.5 to about 7, from about 4.5 to about 6.7, from about 5 to about 7, or from about 5 to about 6.7). Examples of suitable agents include: anesthetics such as bupivacaine, lidocaine, proparacaine, and tetracaine; analgesics, such as acetaminophen, ibuprofen, fluriprofen, ketoprofen, voltaren, phenacetin and salicylamide; anti-inflammatories selected from the group consisting of naproxen and indomethacin; antihistamines, such as chlorpheniramine maleate, phenindamine tartrate, pyrilamine maleate, doxylamine succinate, henyltoloxamine citrate, diphenhydramine hydrochloride, promethazine, brompheniramine maleate, dexbrompheniramine maleate, clemastine fumarate and triprolidine; broad and medium spectrum, fungal medications, monobactams and viral agents and specifically including such as erythromycin, penicillin and cephalosporins and their derivatives.

In some embodiments the additional pharmacologically active agent may be suitable for treating glaucoma. Examples of suitable agentsfor treating glaucoma include beta blockers such as betaxolol, carteolol, levobunolol, timolol; cabonic anhydrase inhibitors such as brinzolamide and dorzolamide; cholinergics such as pilocarpine; prostaglandins such as bimatoprost, latanoprost, tafluprost, travoprost, unoprostone. Further examples include cannabinoids, apraclonidine, brimonidine, dorzolamide, dipivefrin, brinzolamide.

Delivery Carrier

The delivery carriers described herein comprise a cellulosic polymer and an anionic polysaccharide in an aqueous solution.

When combined with an aqueous medium the cellulosic and anionic polysaccharide form a hydrogel when the mixture is brought to an appropriate temperature. The hydrogel remains a liquid at ambient temperatures. On administration to the patient the mixture flows about the area, and, in the warmer environment of the administration site forms a stable hydrogel.

Suitable anionic polysaccharides such as hyaluronic acid (HA) exhibit concentration-dependent gelation and shear-thinning characteristics. Typically, anionic polysaccharide gels lack integrity due to their high hydrophilicity. In contrast, cellulosic polymers such as methylcellulose are highly viscous and form gels in a temperature-dependent manner but do not have fast-gelling properties. As demonstrated herein a delivery carrier of a cellulosic polymer and an anionic polysaccharide (and nanoparticles) can be optimized to achieve a balance between temperature-dependent rheopexy (thickening) and thixotropy (thinning). Using a systematic approach, the inventors have 'tuned' the sol-gel transition temperature to occur at the specific temperature of the ocular surface (i.e. at about 30° C. to about 37° C.). These gelation characteristics permit the hydrogel to form a thin, uniform coating over the cornea through blinking of the eyelid to maintain a pharmacologically active agent (e.g., cannabinoid) in the delivery carrier and in proximity to an area in need of the agent.

Thus, in some embodiments, a delivery formulation (e.g., containing one or more cannabinoids such as CBGA) is provided that is suitable to apply as a liquid to the ocular surface, whereupon the formulation exhibits temperature dependant gel-formation and shear-dependent thinning. In some embodiments, the temperature dependant gel-formation and shear-dependent thinning properties are sufficient to to form a thin, uniform coating over the cornea through blinking of the eyelid. In some embodiments, the temperature-dependent gel-formation and shear-dependent thinning properties increase transcorneal penetration over control formulations (e.g., control formulations comprising, consisting essentially of, or consisting of mineral oil and one or more cannabinoids such as CBGA). Such enhanced transcorneal penetration can provide for at transcorneal penetration of at least 0.2% over four hours, at least 1% over four hours, at least 4% over four hours, from about 0.2% to about 10% over four hours, from about 0.2% to about 5% over four hours, or from about 0.5% to about 5% over four hours.

In some embodiments, the formulation provides delivery of drug active to the lens that is at least 50% higher, 75% higher, or at least 2-fold the delivery provided by a control formulation (e.g., a control formulation comprising, consisting essentially of, or consisting of mineral oil and one or more cannabinoids such as CBGA), e.g., after four hours. In some embodiments, the formulation provides delivery of drug active to the lens that is from about 50% higher to about 2-fold higher, or from about 75% higher to about 2-fold higher than the delivery provided by a control formulation (e.g., a control formulation comprising, consisting essentially of, or consisting of mineral oil and one or more cannabinoids such as CBGA), e.g., after four hours. In some embodiments, the formulation provides delivery of drug active to the cornea that is at least 50% higher, 75% higher, at least 2-fold, or at least 4-fold the delivery provided by a control formulation (e.g., a control formulation comprising, consisting essentially of, or consisting of mineral oil and one or more cannabinoids such as CBGA), e.g., after four hours. In some embodiments, the formulation provides delivery of drug active to the cornea that is from about 50% higher to about 4-fold higher, from about 75% higher to about 4-fold higher, or from about 100% higher to about 4-fold higher than the delivery provided by a control formulation (e.g., a control formulation comprising, consisting essentially of, or consisting of mineral oil and one or more cannabinoids such as CBGA), e.g., after four hours.

In some embodiments the cellulosic polymer or the anionic polysaccharide are biocompatible, mucoadhesive or both.

Suitable cellulosic polymers include methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, hydroxypropyl methylcellulose acetate, hydroxypropyl methylcellulose propionate, hydroxypropyl methylcellulose butyrate, carboxymethylcellulose, derivatives of cellulose polymers, and any mixture thereof.

Suitable anionic polysaccharides include hyaluronic acid, derivatives of hyaluronic acid, alginate, derivatives of alginate, chitosan, derivatives of chitosan, and any mixture thereof.

The delivery carrier is based on an aqueous medium. In a one embodiment, the aqueous medium is saline, buffered saline or water.

As set out in Example 9 the concentration of cellulosic polymer and nanoparticle size affect the gel point of the delivery carrier. For example increasing the concentration of the cellulosic polymer results in lower gel points (gels at cooler temperatures) while delivery carriers containing larger particles form gels at higher temperatures.

In order to determine the gel point for a given composition the following polynominal equation, relating the gel point (T) to three influential factors, was developed:

$$T = 56.32 + 3.09 X_{AP} - 4.98 X_{CP} + 5.23 X_{NP} - 2.25 X_{AP} X_{CP} - 2.86 X_{MP} X_{NP}$$

Where $X_{AP}$ is the concentration of anionic polysaccharide, $X_{CP}$ is the concentration of cellulosic polymer and $X_{NP}$ is average nanoparticle diameter. Using this equation it can be seen that an optimal composition for T=at about 30° C. to about 37° C. For example an optimal composition for T=32° C. may be composed of the following: HA concentration of 1.5 wt %, MC concentration of 2.5 wt %, and NP diameter: 200 nm. Given the relationship between each of $X_{AP}$, $X_{CP}$ and $X_{NP}$ if one changes then each of the others would also need to change to produce a delivery carrier with a specific gel point, for example 32° C. The gel point can be checked using a rheometer or any method known in the art.

Suitable gel-points for the formulations are those that are substantially the same as the temperature of the part of the body they are intended to be administered to. For example the temperature of the surface of the eye is about 32° C., skin temperature is about 34° C. while normal body temperature is 37 while normal body temperature is 37° C. Accordingly gel points for the formulations can range from about 30° C. to at least 40° C. For example suitable gel points include 30° C., 30.25° C., 30.5° C., 30.75° C., 31° C., 31.25° C., 31.5° C., 31.75° C., 32° C., 32.25° C., 32.5° C., 32.75° C., 33° C., 33.25° C., 33.5° C., 33.75° C., 34° C., 34.25° C., 34.5° C., 34.75° C., 35° C., 35.25° C., 35.5° C., 35.75° C., 36° C., 36.25° C., 36.5° C., 36.75° C., or at least about 37° C.

In some embodiments the concentration of cellulosic polymer is about 0.2 wt % to about 10 wt % of the formulation. For example the concentration of cellulosic polymer may be about 0.2, 0.4, 0.6, 0.8, 1.0, 1.25, 1.5, 1.75, 2.0, 2.25, 2.5, 2.75, 3.0, 3.25, 3.50, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, or about 10.0 wt % of the formulation.

In some embodiments the concentration of anionic polysaccharide is about 0.1 wt % to about 10 wt % of the formulation. For example the concentration of anionic polysaccharide may be about 0.1, 0.2, 0.4, 0.6, 0.8, 1.0, 1.25, 1.5, 1.75, 2.0, 2.25, 2.5, 2.75, 3.0, 3.25, 3.50, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, or about 10.0 wt % of the formulation.

In some embodiments the weight ratio of cellulosic polymer to anionic polysaccharide can be in the range of about 1.1:1 to about 10:1, including any integer between 1.1 and 10 for the first numerical value in the ratio.

It will be understood by those skilled in the art that the ranges and ratios stated above are approximate, and may depend on the choices of each polymer as well as on the rheological, gelation and degradation properties desired in the delivery carrier product, and the diameter of the nanoparticles.

In accordance with one embodiment the delivery carrier composition is prepared by wetting a cellulosic polymer such as methylcellulose with hot aqueous medium (for example water or buffered saline) and with agitation. The aqueous medium may be at a temperature of 40-99° C. Suitable temperature for the hot aqueous medium are 40° C., 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99° C. Additional aqueous medium (not heated) is then added an the temperature lowered to about 0° C. and agitation is continued before adding the anionic polysaccharide (such as hyaluronic acid) after which agitation is continued.

In one embodiment, the aqueous medium is water or buffered saline solution.

In another embodiment of the method, a portion of the cellulosic polymer can be added before the anionic polysaccharide is added. In one embodiment a quantity of anionic polysaccharide is added to a quantity of aqueous medium in a vessel at ambient temperature and stirred until it is dissolved. The solution is then heated, for example to about 90° C. and a desired quantity of cellulosic polymer is added to the vessel.

In another embodiment, the cellulosic polymer is added to a portion of the aqueous medium at an elevated temperature with mixing to ensure that the cellulosic polymer aggregates are thoroughly wetted and dispersed. The remaining solvent is then added at a lower temperature to promote solubility of the powder in the aqueous solvent. The vessel is then cooled, and an amount of anionic polysaccharide is added as a solid or as a solution. The contents are mixed, and the vessel is cooled. Cold or ambient temperature aqueous medium is then added with mixing to adjust the concentration of the polymers to the desired level.

The delivery carriers described herein are biocompatible and do not require the introduction of chemical cross-linkers or free radicals. The delivery carriers described herein may be safely administered to many areas of the body, including, for example the eye.

Dosage Forms

The formulations may be administered using any known dosage form. The formulations are particularly well suited to topical administration including administration to the eye. Suitable ocular dosage forms include liquids, suspensions, emulsions, gels, creams and pastes. Typically the ocular dosage is the liquid formulation with suspended nanoparticles containing a pharmacologically active agent.

Methods of Treatment

The formulations described herein are typically packaged as a liquid and applied as an eye drop. The liquid will form a gel when its temperature is elevated to body temperature.

The methods of treatment using the formulations typically require administering the formulation to the eye of a patient. A typical protocol for use of the formulation as eye drops to treat or to alleviate the symptoms of an eye disorder is to place at least one drop of the formulation in the affected eye at least once daily until the severity of the symptoms is reduced to an acceptable level. In particularly severe eye disorders, more frequent applications may be necessary. For example the formulation may be administered, for example 1, 2, 3, 4, 5, 6, 7, 8, 9 or 10 times daily.

In one embodiment, the formulations are capable of improving the concentration of the pharmacologically active agent (e.g., cannabinoid) in an environment relative to a control formulation. In order to determine concentration enhancement in vitro, the amount of pharmacologically active agent (e.g., cannabinoid) in the nanoparticles is measured. The formulation provides a concentration enhancement if, when administered to an eye it provides a pharmacologically active agent (e.g., cannabinoid) concentration in any part of the eye that is at least 1.2-fold the free pharmacologically active agent (e.g., cannabinoid) concentration provided by the control formulation.

The pharmacologically active agent (e.g., cannabinoid) concentration provided by the formulations may be at least about 1.5-fold, at least about 2-fold, or at least about 3-fold that provided by the control formulation. The pharmacologically active agent (e.g., cannabinoid) concentration provided by the formulations may be from at least about 1.5-fold to at least about 5-fold, from at least about 1.5-fold to no more than about 5-fold, from at least about 1.5-fold to no more than about 6-fold, from at least about 1.5-fold to no more than about 10-fold, from at least about 2-fold to no more than about 5-fold, from at least about 2-fold to no more than about 10-fold, from at least about 3-fold to no more than about 5-fold, or from at least about 3-fold to no more than about 10-fold that provided by the control formulation.

Alternatively, the formulations described herein, when applied to the eye, provide an AUC in pharmacologically active agent (e.g., cannabinoid) concentration in any eye tissue or fluid that is at least 1.2-fold that observed with the control formulation. The AUC may be at least about 2-fold, at least about 3-fold, at least about 4-fold, at least about 5-fold, at least about 6-fold, yet more preferably at least about 10-fold, or at least about 20-fold that of the control formulation.

When applied to the eye, the formulations described herein can deliver a local active concentration of the pharmacologically active agent (e.g., cannabinoid) in the eye tissue or fluid that is at least a 1.5-5-fold improvement over the control. In some cases, the improvement is at least about 1.5-fold, at least about 2-fold, or at least about 3-fold that provided by the control formulation. In some cases, the improvement is from at least about 1.5-fold to at least about 5-fold, from at least about 1.5-fold to no more than about 5-fold, from at least about 1.5-fold to no more than about 6-fold, from at least about 1.5-fold to no more than about 10-fold, from at least about 2-fold to no more than about 5-fold, from at least about 2-fold to no more than about 10-fold, from at least about 3-fold to no more than about 5-fold, or from at least about 3-fold to no more than about 10-fold that provided by the control formulation.

In another embodiment, the formulations, when administered to the eye, provide a maximum cannabinoid concentration in any tissue or fluid of the eye ($C_{max}$) that is at least 1.2-fold that observed with the control formulation. Preferably, the $C_{max}$ is at least about 2-fold, at least about 3-fold, at least about 4-fold, at least about 6-fold, at least about 10-fold, or at least about 20-fold that of the control formulation. In another embodiment, the formulations, when administered to the eye, provide a maximum cannabinoid concentration in any tissue or fluid of the eye ($C_{max}$) that is 1.2-fold that observed with the control formulation. Preferably, the $C_{max}$ is about 2-fold, about 3-fold, about 4-fold, about 6-fold, about 10-fold, or about 20-fold that of the control formulation.

In another embodiment, the formulations, when administered to the eye, provide a maximum cannabinoid concentration in any tissue or fluid of the eye ($C_{max}$) that is at least about 1.2-fold and no more than about 20-fold, at least about 1.2-fold and no more than about 10-fold, at least about 1.2-fold and no more than about 5-fold, at least about 1.5-fold and no more than about 20-fold, at least about 1.5-fold and no more than about 10-fold, at least about 1.5-fold and no more than about 5-fold, at least about 2-fold and no more than about 20-fold, at least about 2-fold and no more than about 10-fold, at least about 2-fold and no more than about 5-fold, at least about 3-fold and no more than about 20-fold, or at least about 3-fold and no more than about 10-fold, at least about 3-fold and no more than about 5-fold that observed with the control formulation.

The present invention will now be further described in greater detail by reference to the following specific examples, which should not be construed as in any way limiting the scope of the invention.

EXAMPLES

Example 1—Materials

Sodium hyaluronate (Mw 752 kDa) was purchased from Lifecore Biomedical LLC. (Chicago, IL, USA). MC A15 PREM LV was obtained as a gift from Dow Chemical (Michigan, USA). Poly(ethylene oxide-b-lactide) (PEO-b-PLA), (5.0-b-23.0) was obtained from Polymer Source Inc. (Montreal, Canada). Carboxy-functionalized poly(styrene) nanoparticles were purchased from Phosphorex (Hopkinton, MA) and used as received. Most of these polymers are available as pharmaceutical grade. Moreover, both, PEO and PLA can be individually purchased as pharmaceutical-grade polymers. PEO is marketed by Dow as POLYOX and Corbion makes pharmaceutical-grade lactic acid under the brand name of PURAC. The synthesis of PLA from LA can be achieved using GMP protocols and the block polymer can subsequently be manufactured using a similar, GMP-approved process.

Cannabigerolic Acid (CBGA, Mw 365 kg/mol) was synthesized chemically as described previously. Water was distilled and deionized using Millipore Milli-RO 10 Plus and Milli-Q UF Plus (Bedford, MA) at 18 MΩ resistance. Simulated tear fluid (STF) was prepared according to previously published protocols (Hägerström, et al. Eur. J. Pharm. Sci. 9, 301-309 (2000)). All organic solvents used were HPLC grade and purchased from Aldrich. All other materials were also purchased from Aldrich and used as received.
Methods Example 2—Preparation of Nanoparticle Loaded Delivery Carriers MC was dissolved in half amount of DI water needed, as hot solvent (90° C.) and agitated until all particles were wetted. The remainder of water was added as cold water to MC solution under stirring. The solution temperature was lowered to 0° C. and agitation was continued for another 15 minutes. The required amount of HA powder was added to this solution and stirring continued for another 10 minutes. Finally the required amount of nanoparticle (NP) suspension was added to make for a final concentration of 10% NP inside the formulation. This mixture was left in the fridge overnight prior to any experiment.

Example 3—Rheological Experiments

A Physica MCR-501 rheometer (Anton Paar, VA, USA) coupled with a cone and plate geometry with 4° angle and 25 mm diameter (CP 25-4) was used to perform all experiments. Silicon oil was utilized to minimize dehydration of the sample during experiments. To identify the range of strain and frequency associated with linear viscoelastic region, an amplitude sweep was performed prior to any experiment. The temperature for sol-gel transition of formulations was identified through performing oscillation experiments and monitoring storage (G') and loss (G") moduli during temperature sweeps. Temperature was increased by a rate of 1° C./min, while the frequency was set at 1 Hz. The gel point was marked as the temperature at which the values for G' and G" start to equate. Shear-thinning behaviour of formulations was also investigated through measuring viscosity as a function of shear rate ranging from 0.01 s$^{-1}$ to 100 s$^{-1}$.

Example 4—Factorial Design for Optimization of Temperature-Sensitive Delivery Carrier Composition In order to identify the optimum composition for the formulation which yields a gel point at 32° C. (i.e. temperature of the ocular surface), a factorial design approach was utilized. The most important factors affecting gel structure of HAMC-NP composites are known to be HA concentration, MC concentration, and NP diameter. Hence, the optimum level of each of these factors were identified through a three-factor, three-level factorial design. The three independent variables (HA concentration ($X_{HA}$), MC concentration ($X_{MC}$), and NP diameter ($X_{NP}$)) were studied at three different levels coded as −1, 0, and 1. There is a specific range of values that a factor can take, i.e. an interval [L;U]. Levels of that factor can then be the lowest and highest values, L and U, along with the middle point, M=L+U. A stability study was ran on HA-MC gels with different concentration ratios and the range of values for HA and MC concentrations was identified based on sample's degradation time. As the intended time window for application of this formulation is patient's bedtime; highest and lowest concentrations which yielded a less than 8-hour degradation time in STF were picked as L and U levels. As for the NP diameter, the range of values was identified based on their optimum size for corneal penetration and lack of irritancy. The dependent variable was the gel point of formulation (represented by temperature) measured by rheometer. The order of runs for experiments did not follow any particular pattern. The function fac.design( ) embedded in DoE.base package of statistical software R was used to generate random order of runs. For a full factorial design, 3$^3$=27 experiments were required. The values for coded and actual variables are presented in Table 1.

TABLE 1

Coded levels and actual composition of formulations used to develop the factorial design.

| Coded variable | Actual variable | Coded levels of factors | | |
|---|---|---|---|---|
| | | −1 | 0 | +1 |
| | | Actual values of factors | | |
| $X_{HA}$ | HA concentration (wt %) | 0.5 | 1 | 1.5 |
| $X_{MC}$ | MC concentration (wt %) | 0.5 | 1 | 1.5 |
| $X_{NP}$ | NP size (nm) | 50 | 100 | 200 |

The effects and interactions between variables were obtained using R. The significance of the variable effects as well as their interaction effects was evaluated by analysis of variance (ANOVA) for each parameter (statistically significant was considered for results with a P value less than 0.5). In a factorial design, usually the goal is to find the setting that produce an optimal output (max or min). However, in this case an output that yields a specific result (32° C.) is desired. Since this output is not a min or max, there could be many possible combinations that yield 32 degrees. After determining the impact of each variable on the output, utilizing the "predict" function in R, the optimum compositions which will undergo gel formation at about 32° C. were identified.

It is important to note that for factorial design experiments, carboxy-functionalized poly styrene beads were utilized, as their diameter and size distribution could be precisely controlled. Once the optimum NP size was identified, the biodegradable nanoparticles were manufactured using PEO-b-PLA, as described in the following section.

Example 5—Preparation of Pharmacologically Active Agent-Loaded PEO-b-PLA Nanoparticles Formation of CBGA-loaded NPs were carried out using the nanoprecipitation method. Briefly, the required amounts of polymer and cannabinoid were dissolved in 10 ml of ethyl acetate (organic phase) either with or without sonication. The organic phase was then added drop-wise to 100 ml of rapidly stirring water and left uncovered for 3 h to allow evaporation of ethyl acetate. NPs were extracted by ultrafiltration (8 min, 4000 g, Amicon Ultra-15, molecular weight cut-off of 30 kDa, Millipore, Billerica, MA, USA). The concentrated NP suspension was washed with water and collected likewise.

Example 6—Physicochemical Characterization of CBGA-Loaded PEO-b-PLA NPs

The particle size and polydipersity index was measured using a Malvern Zetasizer Nano ZS (Malvern, Westborough, Massachusetts) at 25° C. and at a scattering angle of 90°.

The morphological evaluation was performed using Scanning Electron Microscopy (Jeol-JSM-6400 Electron Microscope Tokyo, Japan). For SEM examination the samples were placed onto aluminium stubs and sputter-coated with gold (Emitech K550X, Eitech Ltd, UK).

Atomic force microscopy measurements were carried out using Multimode 8 Scanning probe microscope (Veeco). A 10 μl sample drop of formulation was spotted on freshly cleaved mica and spread over surface to form a thin film of sample. The film was allowed to air dry and immediately observed by AFM to record topographical images.

For calculation of encapsulation efficiency (EE), equation (1) was used. 1 ml of acetonitrile was added to the nanosuspension obtained after ultrafiltration and washing steps. This mixture was sonicated using a 100 W sonicator (Sonic Dismembrator; Fisher Scientific) for 1 min over an ice bath. The amount of encapsulated cannabinoid was identified through HPLC analysis. The instrument was equipped with a UV detector and a reverse-phase C-18 column. An isocratic mobile phase of water: acetonitrile 15:85 and 0.01% Trifluoroacetic acid (TFA) at a constant flow rate of 1 mL/min and temperature of 40° C. was used. The peak was measured at a wavelength of 270 nm. For an injection volume of 10 μL, the retention time was ~9 min.

$$\text{Encapsulation Efficiency}(EE) = \frac{\text{actual drug:polymer ratio}}{\text{Initial drug:polymer ratio}} \times 100 \quad (1)$$

Cannabinoid loading (DL) was calculated using the following equation:

$$\text{Drug Loading}(DL) = \frac{\text{Mass of encapsulated drug}}{\text{Mass of recovered } NP} \times 100 \quad (2)$$

Example 7—In Vitro Release

The in vitro cannabinoid release behavior of optimized HAMC-NP formulations was assessed using 7000 MWCO Slide-A-Lyzer Mini Dialysis Units (Thermo Scientific). A 40 μL aliquot of formulation was injected into the dialysis unit using an 18 G needle and the samples were dialyzed against 4 L of STF at 32° C. with constant stirring. At predetermined time intervals, 3 dialysis units were removed from STF and their content was analyzed by HPLC (using the method described above) to determine their cannabinoid content. Amount of cannabinoid released was calculated by subtracting this number from initial cannabinoid loading.

Example 8—Corneal Penetration

In order to examine the ocular penetration of cannabinoid through HAMC-NP formulation, freshly excised porcine eye balls (obtained from center for comparative medicine, University of British Columbia) were used. Franz diffusion cell technique (with fully dissected cornea mounted as the membrane) was avoided, due to experimental pitfalls associated with this method, namely corneal swelling. The eyeballs used in this study were obtained with the eyelid on the top in order to preserve the corneal integrity and ensure the proximity of experimental conditions to in vivo state. Each eyeball was placed into a concave-shaped construct made of plasticine clay. The plasticine surface was covered with cling film prior to placing the eyeball inside. The Franz cell's donor compartment was placed right on top of the cornea and was secured using the cling film. 40 μL of either CBGA loaded HAMC-NP formulation or control formulation (CBGA dissolved in light mineral oil) was added to the donor cell. This construct was placed in a water bath at 32° C. After 4 h treatment, the formulations were removed from corneal surface and were washed with STF. The cornea and lens were dissected and added to 1 ml of methylene chloride. After 4 h incubation at 60 degrees, the vials containing digested tissues were centrifuged and the supernatant was analyzed for extracted CBGA content using HPLC.

Results and Discussion

Example 9—Optimization of HAMC-NP Composite

The influencing factors that might affect gel properties of HAMC-NP composite systems are thought to be HA concentration (HA wt %), MC concentration (MC wt %) and NP size. Initially, to confirm that gel point can be controlled through polymer concentrations in the composite system, a set of rheology experiments were performed. A representative graph is shown in FIG. 1 and it can be seen that the gel point can be modulated using polymer concentration ratios inside the composite.

Figure 2:
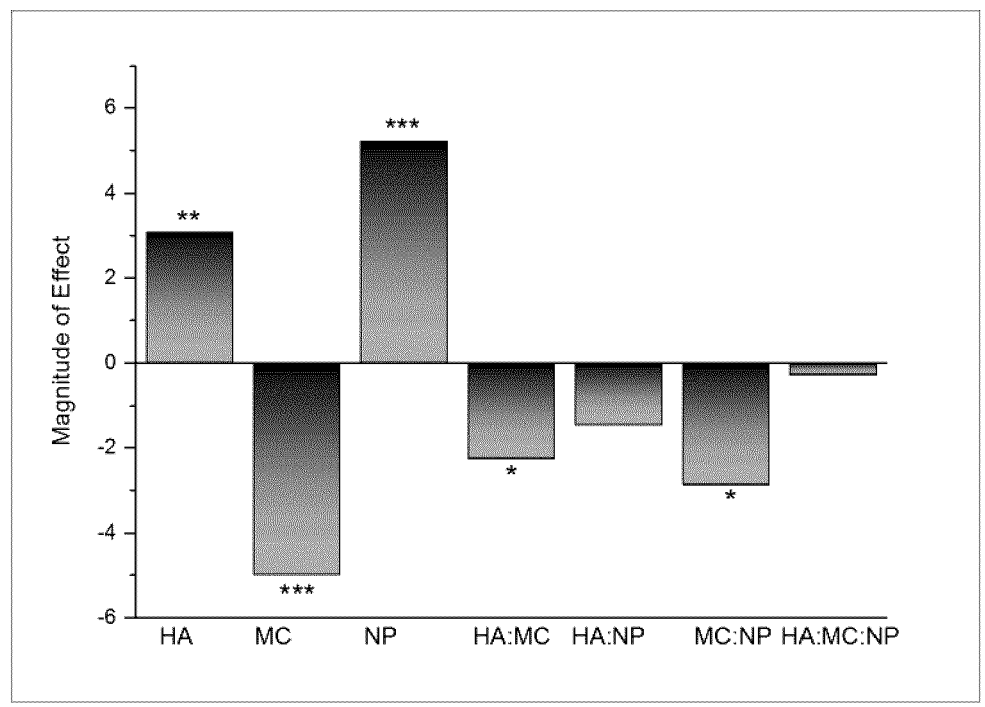
FIG. 2. Pareto plot for evaluation of the effect of independent variables (HA concentration, MC concentration, nanoparticle (NP) size) and their interactions on gel point of HAMC-NP composites systems (Statistical Significance codes: P value 0 '*', 0.001 '', 0.01 '*').

In order assess the impact of each factor in a more quantitative manner and design a composite system with a gel point equal to temperature of ocular surface (32° C.), a $3^3$ factorial design based on three independent variables was utilized to plan the rest of the experiments. A total of 27 rheological experiments were performed looking at the gel point of HAMC-NP composites. The Pareto plot displayed in FIG. 2, demonstrates the effects of each individual factor as well as interaction between different factors on the gel point of the composites.

The results obtained in factorial design indicated that MC (wt %) and NP size can significantly affect the gel point of the composites in two opposite manner. As exhibited in Pareto plot (FIG. 2), increasing the MC content of composite results in lower gel points (cooler temperatures). As described earlier, the temperature-sensitivity of HAMC-NP composites stems from temperature-sensitive nature of MC. Hence, an increase in number of entanglements among MC polymer chains (at higher concentrations) would result in lower levels of energy required for gel formation (i.e. lower gel point temperatures). On the other hand, the composites containing larger particles undergo sol-gel transition at higher temperatures. This might be due to the fact that larger particles hinder MC polymer chain entanglements to a large extent; hence a higher level of internal energy (associated with higher temperatures) is required for sol-gel transition in such systems. Another significant factor influencing the gel point of the composites was found to be HA concentration.

Through this factorial design and excluding the effects which were not statistically significant (i.e. HA:NP, and HA:MC:NP) the following polynominal equation, relating the gel point (T) to three influential factors, was developed:

$$T = 56.32 + 3.09 X_{HA} - 4.98 X_{MC} + 5.23 X_{NP} - 2.25 X_{HA} X_{MC} - 2.86 X_{MC} X_{NP} \quad (3)$$

Figure 3:
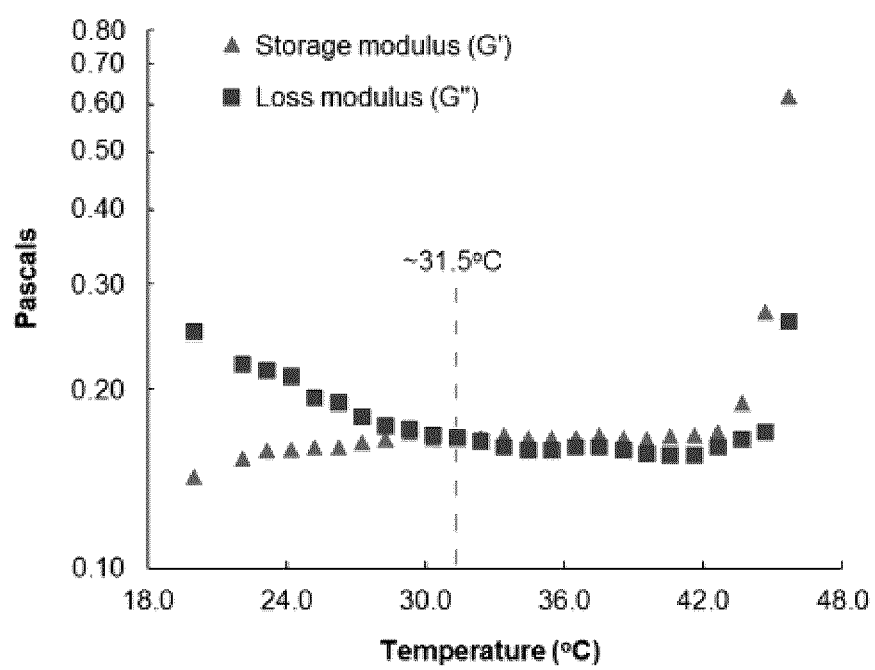
FIG. 3. Temperature sweep on optimized formulation shows occurrence of gel point at a temperature close to that of ocular surface.

Utilizing the "predict" function on the developed model for T (equation 3), it can be concluded that an optimal composition for T=32° C. may be composed of the following: HA concentration of 1.5 wt %, MC concentration of 2.5 wt %, and NP diameter: 200 nm. This optimal formulation was then produced and its gel point was checked using a rheometer. The graph is presented in FIG. 3 and confirms sol-gel transition of the formulation at the desired temperature.

Example 10—Physicochemical Characterization of CBGA-Loaded PEO-b-PLA NPs

The influence of polymer composition, CBGA loading and sonication on the size distribution of PEO-b-PLA NPs prepared via nanoprecipitation was investigated and revealed that setting an initial polymer concentration of 5 mg/mL in the organic phase, having a cannabinoid loading of 2% and excluding the sonication step in the workflow resulted in the synthesis of NPs with an average diameter of 186 nm and a PDI of 0.118. This size is close to the optimal NP diameter identified through factorial design. The impact of different manufacturing steps are exhibited in FIG. 4.

Size distribution of Poly(ethylene oxide-b-lactide) (PEO-b-PLA) nanoparticles (NPs) prepared under different manufacturing conditions as set out in Table 2.

TABLE 2

Figure 4:
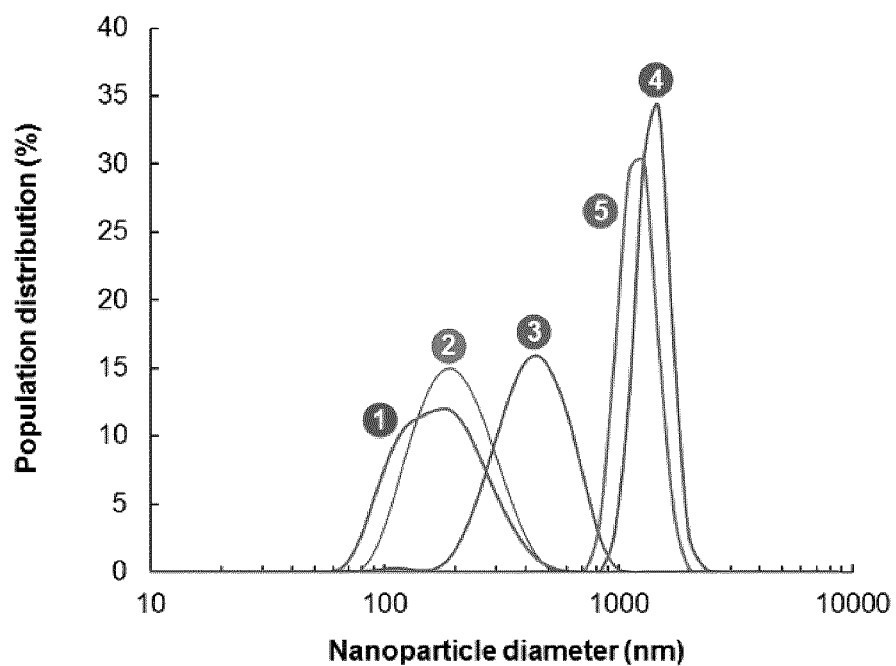
FIG. 4. Size distribution of Poly(ethylene oxide-b-lactide) (PEO-b-PLA) nanoparticles (NPs) prepared under different manufacturing conditions as set out in Table 1.

Manufacturing conditions PEO-b-PLA NPs in FIG. 4

| Curve number | Polymer conc. (mg/mL) | Cannabinoid loading (%) | Sonication |
| --- | --- | --- | --- |
| 1 | 5 | 0 | No |
| 2 | 5 | 2 | No |
| 3 | 10 | 0 | No |
| 4 | 5 | 0 | Yes |
| 5 | 10 | 0 | Yes |

As shown in FIG. 4, sonication of organic phase resulted in disruption of core-shell structures and caused the size to increase dramatically. Freeze-drying has also had the same impact (results not shown. It was also found that incorporation of 2% CBGA in NP structures caused their diameter to increase very slightly.

Figure 5:
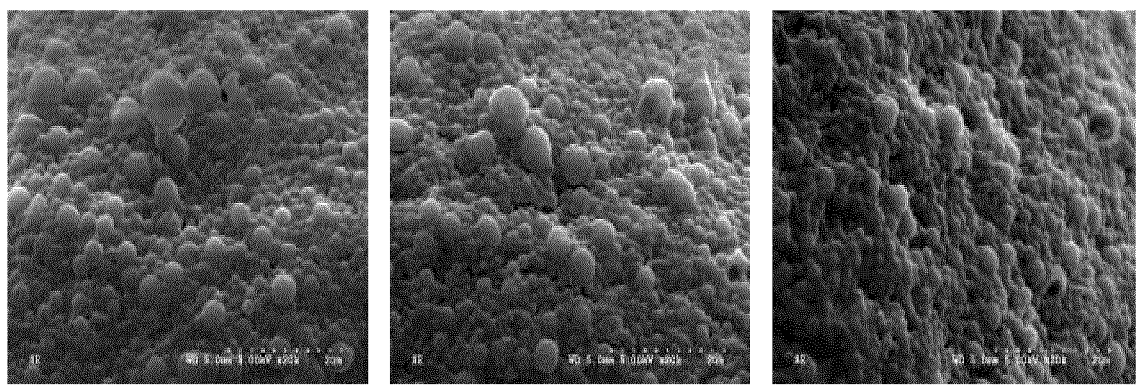
FIG. 5. Three images of nanoparticles from different areas of the cannabinoid formulation sample, acquired through scanning electron microscopy at a working distance of 5.0 mm and an accelerating voltage of 5.00 kV.

Morphology of PEO-b-PLA NPs was studied by SEM. The nanoparticle size distribution was determined using Scanning Electron Microscopy (S-3000N Scanning Electron Microscope, Hitachi, Tokyo, Japan). A small sample was placed onto a bare aluminum stub and allowed to air dry. The sample was then sputter-coated with 5 nm of gold-palladium alloy (Desk II Sputter Coater, Denton Vacuum Inc., Moorestown, NJ, USA). A working distance of 5.0 mm and an accelerating voltage of 5.00 kV were used to image the sample. Six images were captured from different parts of the sample, three of which are shown below in FIG. 5. Image-J software (National Institute of Health, Bethesda, Maryland, USA) was used to measure the diameters of the nanoparticles. 20 particles from each of the six images were selected at random and measured, as well as all the particles in one of the images to ensure reliability of results and to reduce bias. Excel software was then used to generate a size distribution curve, shown in FIG. 4, and calculate distribution statistics. Raw data particles 1.5×IQR (interquartile range) above and below the third quartile and first quartile, respectively, were categorized as outliers and omitted from the distribution. With outliers accounted for, the median and mean particle diameters were determined to be 0.184 nm and 0.196 nm, respectively, with a low standard deviation of 0.0603. There is an insignificant (2%) percentage difference between the optimal and the observed median nanoparticle diameter, as well as an insignificant variance in nanoparticle diameters through the sample.

Figure 6:
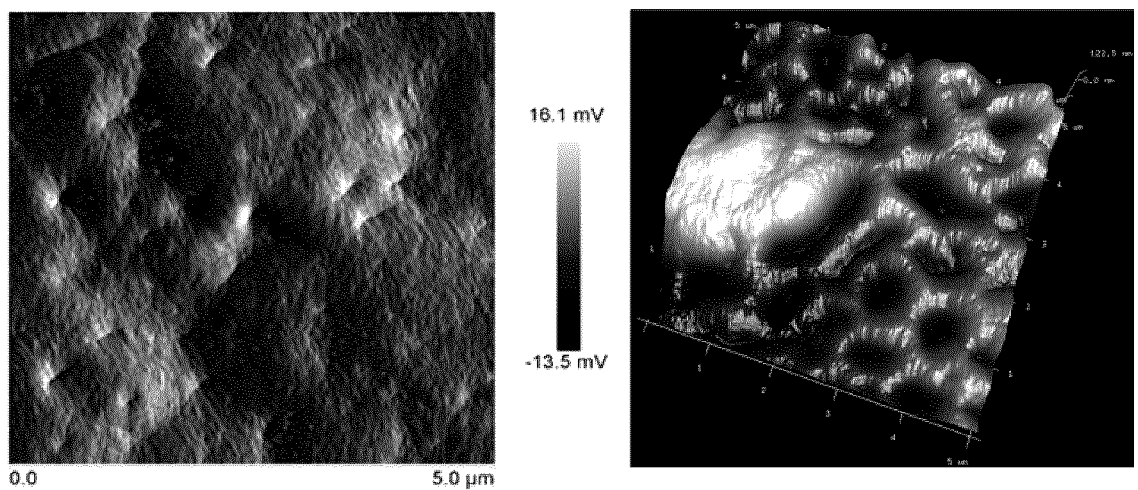
FIG. 6. Atomic force microscopic image of PEO-b-PLA NP formulation.

To gain the topographical insight of PEO-b-PLA NPs formulation, AFM images were obtained in AC tapping mode at 5 μm×5 μm section with tip velocity of 9.8 μm/s and loop gain of 8 using scan speed of 0.977 Hz (FIG. 6). The morphological images reveal that the surface texture is smooth and shows uniform and spherical shaped particles embedded in delivery carrier.

Example 11—Corneal Penetration of CBGA

The method used in this study provides more similarity to in vivo condition compared to conventional Franz diffusion technique. Although, it is important to note that the lack of lachrymal drainage and shear forces associated with blinking might result in some experimental artifacts, the in vivo model used herein is an accepted model system for study of corneal penetration formulations.

In order to examine the ocular penetration of cannabinoid through HAMC-NP formulation, freshly excised porcine eye balls (obtained from center for comparative medicine, UBC) were used. Franz diffusion cell technique (with fully dissected cornea mounted as the membrane) was avoided, due to experimental pitfalls associated with this method, namely corneal swelling. A similar method has also been used by Mun et.al. (Mol. Pharm. 11, 3556-64 (2014)). The eyeballs used in this study were obtained with the eyelid on the top in order to preserve the corneal integrity and ensure the proximity of experimental conditions to in vivo state. Each eyeball was placed into a concave-shaped construct made of plasticine clay. The plasticine surface was covered with cling film prior to placing the eyeball inside. The Franz cell's donor compartment was placed right on top of the cornea and was secured using the cling film. 40 µL of either CBGA loaded HAMC-NP formulation or control formulation (CBGA dissolved in light mineral oil) was added to the donor cell. This construct was placed in a water bath at 32° C. After 4 h treatment, the formulations were removed from corneal surface and were washed with STF. The cornea and lens were dissected and added to 1 ml of methylene chloride. After 4 h incubation at 60 degrees, the vials containing digested tissues were centrifuged and the supernatant was analyzed for extracted CBGA content using HPLC.

Figure 7:
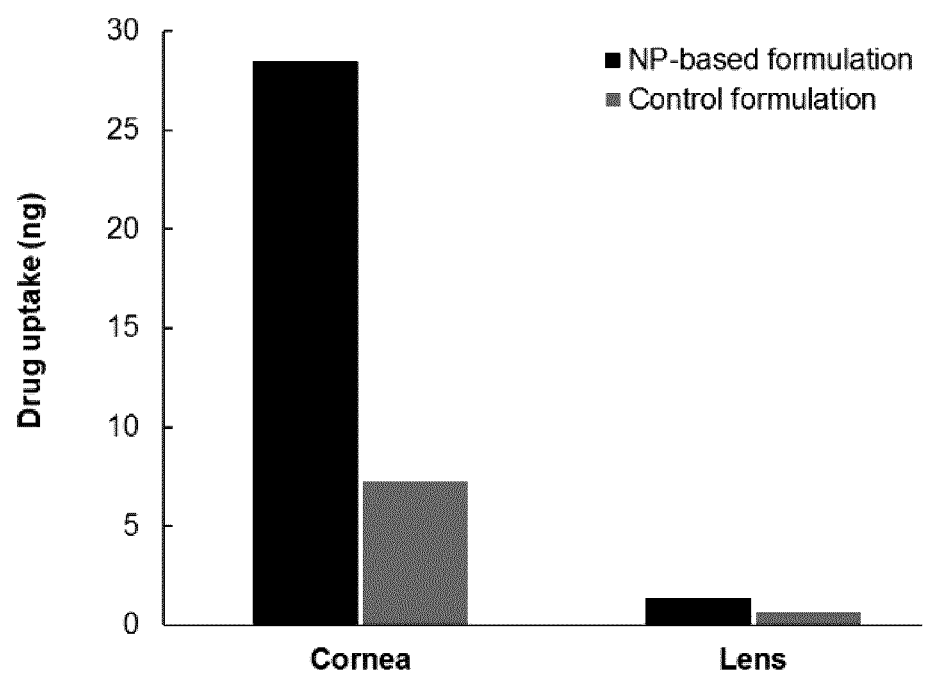
FIG. 7. Cannabinoid uptake by cornea and lens after exposing to corneal surface to either HAMC-NP formulation or the control formulation.

HPLC analysis on dissected cornea and lens after a 4 hour treatment demonstrated impressive uptake of the CBGA (FIG. 7). Not only did the formulation greatly outperform the control formulation, but this study is the first of its kind to report direct CBGA uptake by the cornea and lens from a composite NP-delivery carrier.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An ocular drug delivery formulation comprising:
a delivery carrier comprising from about 1 wt % to about 4 wt % of methyl cellulose as a cellulosic polymer, and from about 0.5 wt % to about 2.5 wt % of hyaluronic acid as an anionic polysaccharide; and
nanoparticles comprising poly(ethylene oxide-b-lactide) as an amphiphilic non-ionizable block copolymer, and a cannabinoid;
wherein:
the formulation has a gel point from about 30° C. to about 34° C.; and
the average diameter of the nanoparticles is from about 75 nm to about 250 nm.

2. The formulation of claim 1 wherein the cannabinoid is selected from the group consisting of cannabigerolic acid (CBGA); cannabigerolic acid monomethylether (CBGAM), cannabigerol (CBG), cannabigerol monomethylether (CBGM), cannabigerovarinic acid (CBGVA), cannabichromevarin (CBCV), cannabichromenic acid (CBCA) cannabichromene (CBC), cannabidiolic acid (CBDA), cannabidiol (CBD), cannabidiol monomethyl ether (CBDM), cannabidiol-C4 (CBD-D4), cannabidivarinic acid (CBDVA), cannabidivarin (CBDV), cannabidiorcol (CBD-D1), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid C4 (THCA-C4), delta-9-tetrahydrocannabinol-C4 (THC-C4), delta-9-tetrahydrocannabivarinic acid (THCVA), delta-9-tetrahydrocannabivarin (THCV), delta-9-tetrahydrocannabiorcolic acid (THCA-C1),), delta-9-tetrahydrocannabiorcol (THC-C1), delta-7-cis-iso-tetrahydrocannabivarin (D7-THCV), delta-8-tetrahydrocannabinolic (D8-THCA), delta-8-tetrahydrocannabinol (D8-THC), cannabicycloic acid (CBLA), cannabicyclol (CBL), cannabicyclovarin (CBLV), cannabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-C4 (CBN-C4), cannabinol-C2 (CBN-C2), cannabivarin (CBV), cannabiorcol (CBN-C1), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CBTVE), dehydrocannabifuran (DCBG), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxy-alpha-alpha-2-trimethyl-9-n-propyl-2,6-methano-2H-1-benzoxoxin-5-methanol (OH-iso-HHCV), cannabiripsol (CBR), and trihydroxy-delta-9-tetrahydrocannabinol (triOH-THC).

3. The formulation of claim 2 wherein the cannabinoid is cannabigerolic acid (CBGA).

4. The formulation of claim 1 wherein the concentration of cellulosic polymer and the average diameter of the nanoparticles determines the gel point of the formulation.

5. An ocular drug delivery formulation comprising:
a delivery carrier comprising 2.5 wt % methyl cellulose and 1.5 wt % hyaluronic acid; and
nanoparticles comprising poly(ethylene oxide-b-lactide) and cannabigerolic acid (CBGA);
wherein the average diameter of the nanoparticles is about 175 nm-200 nm; and
wherein the formulation has a gel point of about 32° C.

6. A method of treatment of an eye disorder comprising administering an effective amount of a formulation of any one of claims 1, 2, 3, 4, and 5 to the eye of a subject in need thereof.

7. The method of claim 6 wherein the eye disorder is glaucoma.

* * * * *